(12) United States Patent
Osaka et al.

(10) Patent No.: US 7,486,403 B2
(45) Date of Patent: Feb. 3, 2009

(54) DROPLET SHAPE MEASURING METHOD AND APPARATUS

(75) Inventors: Tatsuo Osaka, Isehara (JP); Yoshikatsu Okada, Yokohama (JP); Shigeru Yamada, Chofu (JP); Keiji Sakai, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 60 days.

(21) Appl. No.: 11/779,754

(22) Filed: Jul. 18, 2007

(65) Prior Publication Data

US 2008/0018909 A1    Jan. 24, 2008

(30) Foreign Application Priority Data

Jul. 20, 2006    (JP)    ............... 2006-197591

(51) Int. Cl.
*G01B 11/02* (2006.01)
*G01N 21/00* (2006.01)

(52) U.S. Cl. .................. 356/496; 356/239.8

(58) Field of Classification Search ............. 356/239.8, 356/335, 496, 499, 511–514, 517, 521
See application file for complete search history.

(56) References Cited

U.S. PATENT DOCUMENTS

| | | | |
|---|---|---|---|
| 4,842,408 A | 6/1989 | Yoshii et al. | |
| 5,037,202 A * | 8/1991 | Batchelder et al. | 356/336 |
| 5,107,112 A | 4/1992 | Yanagisawa et al. | |
| 5,220,555 A | 6/1993 | Yanagisawa et al. | |
| 5,299,184 A | 3/1994 | Yamano et al. | |
| 5,329,122 A | 7/1994 | Sakai et al. | |
| 5,329,513 A | 7/1994 | Nose et al. | |
| 5,371,727 A | 12/1994 | Shido et al. | |
| 5,414,260 A | 5/1995 | Takimoto et al. | |
| 5,485,451 A | 1/1996 | Yamano et al. | |
| 5,526,334 A | 6/1996 | Yamano et al. | |
| 5,535,018 A | 7/1996 | Yamano et al. | |
| 5,581,364 A | 12/1996 | Hatanaka et al. | |
| 5,604,591 A | 2/1997 | Kitagawa | |
| 5,793,040 A | 8/1998 | Oguchi et al. | |
| 5,831,961 A | 11/1998 | Sakai et al. | |
| 5,835,211 A * | 11/1998 | Wells et al. | 356/336 |
| 5,870,189 A * | 2/1999 | Uesugi et al. | 356/335 |
| 2005/0041041 A1 | 2/2005 | Sakai | |

FOREIGN PATENT DOCUMENTS

| | | |
|---|---|---|
| JP | 8-94444 A | 4/1996 |
| JP | 2001-41724 A | 2/2001 |
| JP | 2002-277216 A | 9/2002 |
| JP | 2005300488 A * | 10/2005 |

* cited by examiner

*Primary Examiner*—Michael A Lyons
(74) *Attorney, Agent, or Firm*—Fitzpatrick, Cella, Harper & Scinto (57) ABSTRACT

In order to accurately measure a shape feature of a minute droplet arranged on a substrate by a simple method, with respect to the droplet, the substrate is perpendicularly irradiated with laser light to cause diffracted light fluxes generated during passage of the laser light through the droplet to interfere with each other, so that a diffraction pattern is obtained. The diffraction pattern formed on a screen of a detector as an image is picked up by an image pickup apparatus. The shape feature of the droplet is measured by using the resultant diffraction pattern and a refractive index of the droplet.

5 Claims, 6 Drawing Sheets

DROPLET SHAPE MEASURING METHOD AND APPARATUS

FIELD OF THE INVENTION AND RELATED ART

The present invention relates to droplet shape measuring method and apparatus for accurately measuring a minute droplet arranged on a substrate by using a diffraction pattern.

In recent years, with size reduction of an electronic device, evaluation of wetting property in an area of 100 μm square or less is becoming important. As a conventional wetting property evaluation method of a base material, there is a method in which evaluation is made by measuring a shape of a droplet added dropwise on a base material to be subjected to evaluation of wetting property.

Generally, in the case of measuring a shape of a droplet by using a contact angle meter, a liquid is added dropwise on a substrate to be measured to form a droplet having a diameter of about 1 mm. Thereafter, an image of the formed droplet is picked up from a direction parallel to the substrate and from the thus picked-up image of the droplet, a shape of the droplet such as a contact angle is measured. In order to perform wetting property evaluation using an area of 100 μm square or less as an object, it is necessary to form a droplet having a diameter of 100 μm or less on the substrate and measure a shape of the droplet.

When the shape of the minute droplet having a diameter of 100 μm or less is measured by the conventional contact angle meter, the droplet as a member to be measured is considerably small compared with an ordinary case, so that an image pickup apparatus of the contact angle meter is required to have a very high resolution. Accordingly, the use of the image pickup apparatus having such a high performance has not been practical in terms of cost.

As a promising method of measuring a shape of a minute object of 100 μm or less, a measuring technique using an interferometer which utilizes a light interference phenomenon has been known. The shape measuring technique using the interferometer utilizes the light interference phenomenon, so that it is possible to measure a shape of an object with an accuracy of light wavelength, i.e., submicrons or less. For this reason, the shape measuring technique using the interferometer has been widely used, as a shape evaluating method of a member to be processed, in a field of semiconductor fine processing or the like.

Principal examples of conventional interferometers for use in a surface shape evaluating method are shown below.

According to a reflection type interferometer described in Japanese Laid-Open Application (JP-A) 2002-277216, first, laser light is caused to obliquely fall on a substrate having a regularly arranged pattern. By analyzing a diffraction pattern generated during the incidence of the laser light, it is possible to measure a thickness of the pattern regularly formed and arranged on the substrate.

In this technique, the diffraction pattern to be generated is subjected to calculation in advance on the basis of optical theory to create an evaluation table and during measurement of the thickness, a thickness for the case of closest diffraction intensity is extracted by looking up the evaluation table.

Further, with respect to a reflection type interferometer described in JP-A 2001-41724, a method utilizing polarized light has been proposed. In this method, a transparent parallel plate arranged in front of a sample is covered with a coating so as to, e.g., reflect an S polarization component of a light beam and allow a P polarization component of the light beam to pass the therethrough, so that laser light incident on the sample is divided into reference light and sample light which are caused to interfere with each other to obtain a diffraction pattern.

In a JP-A Hei 8-94444, a transmission type interferometer has been described. A method of obtaining a phase difference in a phase area from a diffraction pattern formed of transmitted light has been proposed with respect to such an object that a pattern having the phase area causing the phase difference with respect to the transmitted light in a transparent area. In this method, linearly polarized light is caused to pass through a birefringent prism and a condenser lens to be separated into two light fluxes having different polarization directions and the sample is irradiated with the two light fluxes. The two light fluxes passing through the sample are recombined by the birefringent prism to generate an interference image on an imaging surface. A brightness of the interference image varies depending on a phase difference between the two light fluxes, so that it is possible to detect a phase difference on the sample by evaluating the diffraction pattern.

However, the above described surface shape measuring techniques (evaluating methods), for a microprocessing object, utilizing a light diffraction pattern are accompanied with problems described below when they are used for a droplet.

In the technique of JP-A 2002-277216, the laser light is obliquely emitted, so that a portion not irradiated with the laser light is caused to occur in the case of using a droplet as a member to be measured. Accordingly, when the optical system described in JP-A 2002-277216 is applied to shape measurement of the droplet, the shape of the droplet cannot be obtained accurately.

Further, the measuring method employing the phase shift method using the reflection optical system described in JP-A 2001-41724, in order to measure a shape of a member to be measured, it is necessary to measure interference fringes of at least two types by moving the member to be measured or changing a phase of the light incident on the object. For this reason, the measurement requires a time. Accordingly, it is difficult to measure a shape of a minute droplet which is vaporized in several seconds. Further, the measuring method requires a mechanism for moving the member to be measured or a mechanism for changing the light phase, thus also involving problems in terms of cost and complicated apparatus constitution.

Further, in the phase shift method using the transmission optical system described in JP-A Hei 8-94444, it is possible to measure a thickness by the phase difference but it is difficult to measure a shape of such a droplet that a height thereof is abruptly changed with respect to the substrate. Further, this method also requires a time for measurement, a mechanism for moving the member to be measured, or a mechanism for changing the light phase, so that the method involves problems in terms of a measurement type, cost, and complicated apparatus constitution. Accordingly, it was also difficult to quickly and simply obtain a shape of a droplet which was arranged on the substrate and had a diameter of about 20-100 μm.

SUMMARY OF THE INVENTION

A principal object of the present invention is to provide a droplet shape measuring method capable of accurately measuring a shape of a minute droplet, arranged on a substrate and having a diameter of 100 μm or less, with as simple a constitution as possible under a circumference where it was difficult to measure the minute droplet shape by the conventional measuring methods.

Another object of the present invention is to provide a droplet shape measuring apparatus capable of accurately and simply measuring the minute droplet shape.

According to an aspect of the present invention, there is provided a droplet shape measuring method comprising:

a first step of detecting a diffraction pattern produced by mutual interference between diffracted light generated when a substrate is perpendicularly irradiated with laser light so that a droplet arranged on the substrate is irradiated with the laser light; and a second step of measuring a shape feature, such as a contact diameter or a contact angle, of the droplet from a refractive index of the droplet and the detected diffraction pattern.

According to the present invention, it is possible to measure a shape of a droplet having a contact diameter of 100 μm or less.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 1(a) and 1(b) are schematic views for illustrating a droplet shape measuring method using a transmission optical system in Embodiment 1, wherein

DETAILED DESCRIPTION OF THE PREFERRED EMBODIMENTS

Embodiments of the present invention will be described with reference to the drawings.

An optical system in a droplet shape measuring method of a droplet according to the present invention will be described with reference to FIG. 1(a).

Referring to FIG. 1(a), a laser light source 1 having a known phase state is prepared and an optical system 2 capable of adjusting a beam diameter is provided. A substrate 3 is provided perpendicularly to an optical axis. On the substrate 3, a droplet 4 is arranged in advance.

Figure 8:
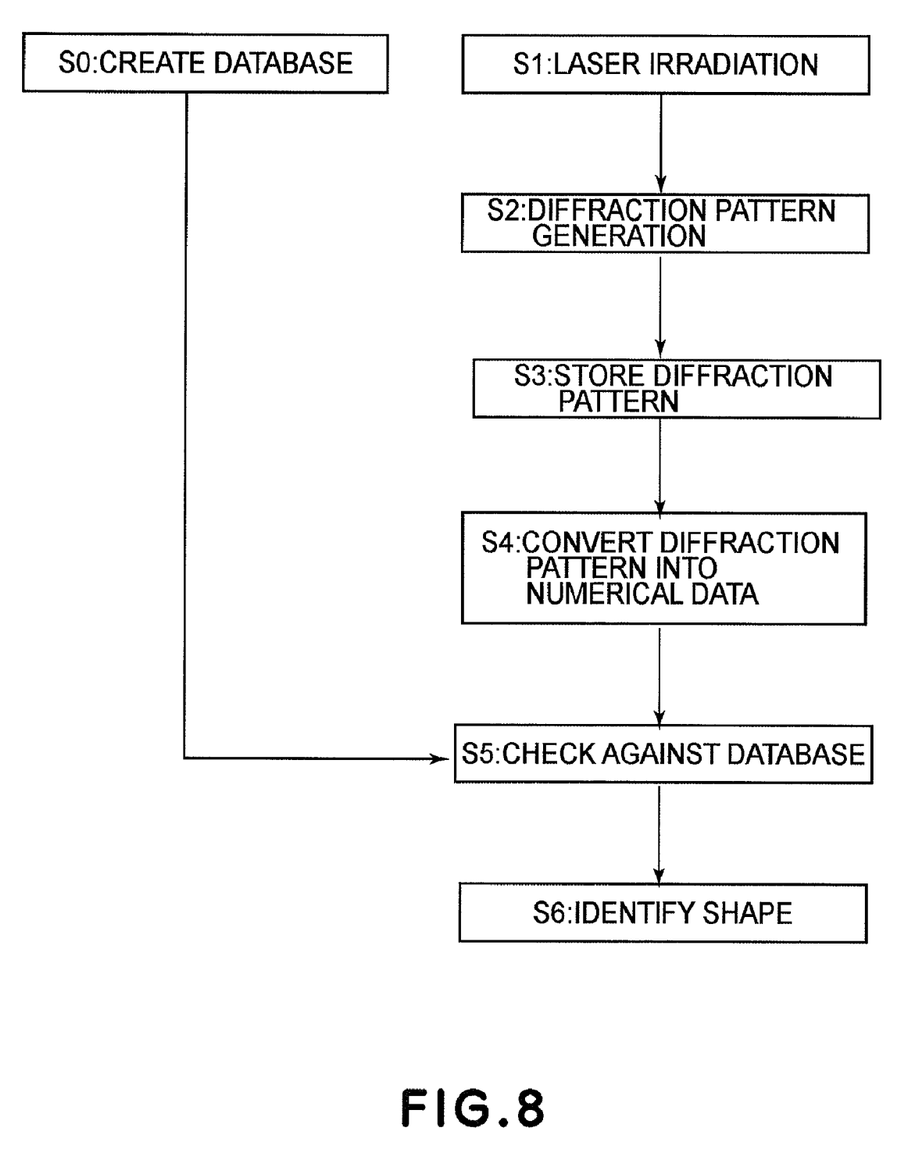
FIG. 8 is a flow chart showing a droplet shape measuring method.

A sequence of the droplet shape measuring method in the present invention will be described with reference to FIG. 8.

First, a step S1 is a step of causing laser light to fall on a measurement substance (a droplet in this embodiment) arranged on the substrate. In a subsequent step S2, a diffraction pattern produced by mutual interference between diffracted light generated by the incident laser light is formed on a screen or the like as an image. In a step S3, by using an image pickup apparatus or the like, a distribution of intensity of the diffraction pattern is recorded. The steps S2 and S3 may also be performed correctively by using an area sensor or the like. In a step S4, the diffraction pattern recorded in the step S3 is inputted into an analyzer to be converted into numerical data. In a step S5, the numerical data for the diffraction pattern converted in the step S4 is compared with diffraction patterns stored in a database created in a step S0 for each of contact diameters, contact angles, and refractive indices prepared in advance by calculation, so that a closest shape value is obtained. In a step S6, the closest shape value in the database is outputted as a measurement result.

In the droplet shape measuring method of the present invention, it is possible to identify (specify) a shape of the measurement substance from the diffraction pattern obtained by irradiating the measurement substance with the laser light through the above described steps.

From the thus measured contact diameter and contact angle, a shape of the droplet arranged on the substrate is determined.

Figure 9:
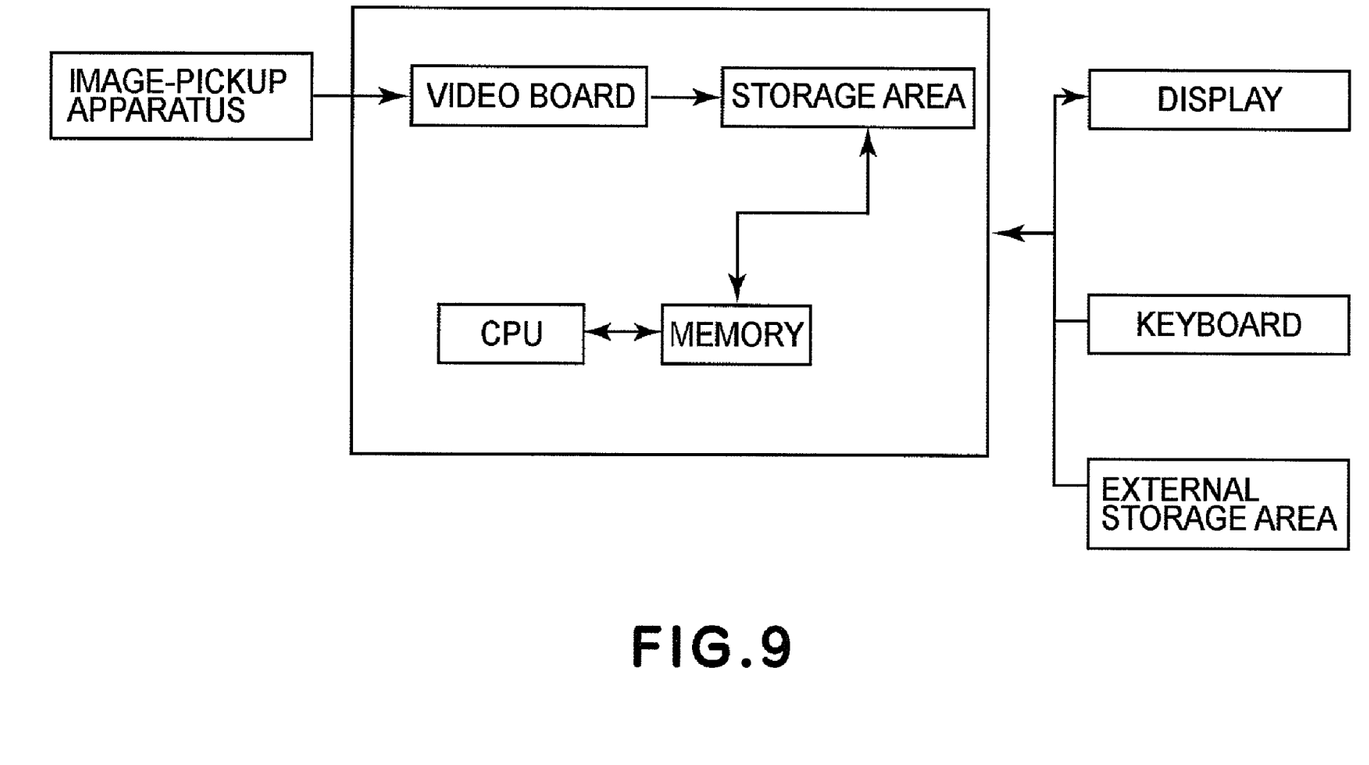
FIG. 9 is a block diagram showing an analyzer.

Next, the analyzer will be described with reference to FIG. 9.

The analyzer utilizes a personal computer including a video board, a CPU, a memory, and a storage area. However, in the case where diffraction patterns are stored in an external storage area in advance, the video board is not essential. To this analyzer, peripheral devices including the image pickup apparatus for obtaining a diffraction pattern, a display for displaying a user interface, a keyboard for performing various inputs, and an optional external storage area are connected. In the thus constituted analyzer, the following processing is effected. First, a diffraction pattern is obtained by the video board of the analyzer and the image pickup apparatus. This diffraction pattern is stored in the storage area. Image data stored in the storage area are stored in the memory by receiving a proper command (instruction) through an input means such as the keyboard and are converted by the CPU into numerical data in a format for use in analysis. The thus converted numerical data are written in the memory and then stored in the storage area. Thereafter, a database is read in the memory.

In this case, the database is stored in the internal storage area of the analyzer or the external storage area. The read database is inputted in the memory. The numerical data to be subjected to analysis are read from the memory into the memory and are checked against the database by the CPU. A most matching result is displayed in the display.

The analyzer has the above described constitution but the present invention is not limited thereto.

With respect to the above described droplet shape measuring method using the transmission optical system according to the present invention, the laser light source will be described more specifically.

First, with respect to the droplet arranged on the transparent substrate, coherent laser light perpendicularly passes through the substrate from a rear side of the substrate.

Generally, laser light incident on an object changes its phase by passing through the object. An amount of the phase change depends on a distance of the object through which the laser light passes and a refractive index of the object. The object passage distance depends on a shape of the object, so that the laser light passes through the object in a state in which it causes a deviation of phase depending on the shape of the object. Phase-deviated waves propagate and planar diffracted light fluxes with a certain distance therebetween interfere with each other to appear as a diffraction pattern. It is possible to measure the shape of the object by analyzing this diffraction pattern.

As the laser light source 1 in the present invention, it is preferable that a laser light source having a known phase state such that it has a phase surface perpendicular to an optical axis at an incident position with respect to the object.

As a type of the laser, there are various types of lasers depending on a laser medium, such as a gas laser, a solid-state laser, and a laser diode but a suitable laser is selected, depending on an absorption spectrum and detecting method of the droplet 4, with respect to a wavelength, a width of the wavelength, a beam shape, a beam intensity, etc. Particularly, it is preferable that a gas laser having a perfect circle as the beam shape and a good beam quality is used.

The laser beam shape may preferably be the perfect circle from the viewpoint of ease of measurement and analysis, depending on the shape of the droplet 4. Further, the beam diameter may preferably be larger than a characteristic length of the droplet 4. The phase state of the laser light may be such that it has a surface perpendicular to an optical axis at a position incident on the droplet 4, so that any of a collimating optical system for changing the light beam to collimated light flux and a light collecting optical system providing a narrowest beam on the substrate 3 may be available. Accordingly, as the optical system 2 for adjusting the laser light, an optical system configured so that the laser light has an equiphase wave surface on the substrate 3 with an arbitrary diameter may be used.

Depending on a state or detecting method of the laser light, the optical system 2 for adjusting the laser light may be omitted.

A material for the substrate 3 is determined whether the optical system is the transmission optical system or the reflection optical system. In the case of the transmission optical system in which the laser light is caused to perpendicularly enter the substrate 3 from a rear side of the substrate 3 and passes through the droplet 4, the substrate 3 is required to be transparent to the laser light used. A surface state of the substrate 3 is of no problem even when a thin film or a pattern is formed at the surface so long as the film or pattern is transparent and has a thickness smaller than a wavelength of the laser light used.

Figure 5:
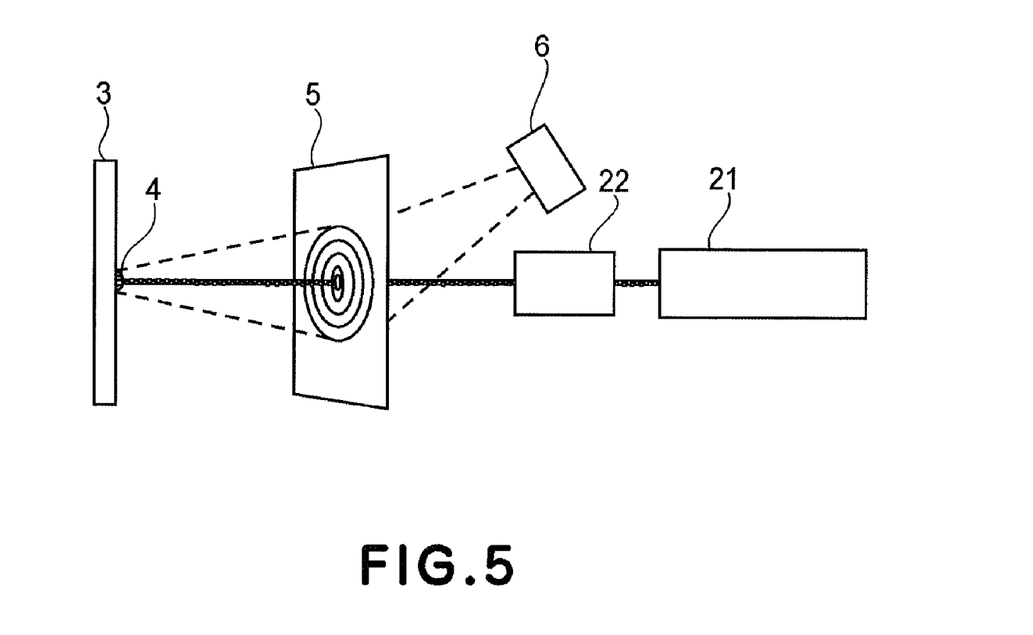
FIG. 5 is a schematic view showing a constitution of a droplet shape measuring apparatus using a reflection optical system in Embodiment 3.

Further, as shown in FIG. 5, in the case of using the reflection optical system which directly irradiates the droplet 4 with laser light from a laser light source 21 through an optical system 22, a kind of and a material for the substrate 3 are not particularly limited so long as a surface roughness of the substrate 3 is smaller than a wavelength of the laser light to such an extent that the substrate 3 excessively absorb the laser light.

However, in the case where a metal film pattern is formed on the surface of the substrate or in the case where the substrate itself has a stepped portion as a structure larger than the wavelength, the metal film pattern or the stepped portion adversely affects the diffraction pattern, so that it is necessary to know a structure of the substrate in advance.

The droplet 4 may be a liquid or soft material consisting of at least one species of component.

A size of the droplet 4 for which the droplet shape measuring method of the present invention is particularly effective is 100 μm or less in contact diameter and a refractive index of the droplet 4 may be known.

As the member to be measured in the present invention, not only the droplet but also any object may be subjected to measurement so long as the object has a shape having axial symmetry with respect to a direction of a normal to the substrate. For example, a microlens or the like is arranged on the substrate and can be subjected to measurement as the member to be measured.

Next, the optical system characteristic to the present invention will be described.

In the present invention, the member to be measured is basically the droplet. The present inventors have found that a basic constitution of the optical system may be such that the laser light perpendicularly enters the substrate on which the droplet (member to be measured) is arranged. This is attributable to the following factors.

First, the transmission optical system will be described. In the transmission optical system, in the case where the laser light is caused to obliquely enter the substrate having thereon the droplet, refraction or scattering during passage of the laser light through the substrate is required to be considered in addition to refracted light by the droplet. Therefore, compared with the case of perpendicular incidence of the laser light, the number of parameters used for analysis is increased. Further, a distribution of intensity of a diffraction pattern to be observed is not concentric circles and is complicated, so that the number of data to be calculated is also increased. For these reasons, the oblique incidence of the laser light in the transmission optical system leads to increases in measurement and analyzing times and a complicated step, thus being unsuitable for practical use.

Next, the reflection optical system will be described. In the case where the laser light is caused to obliquely fall on the droplet in the reflection optical system, due to the droplet shape, a portion which is not irradiated with the laser light is present in some cases. Further, when an angle of the incident light is not larger than a contact angle of the droplet, reflected light at the droplet surface on the light incidence side does not reach a detecting surface. Accordingly, when the laser light is caused to obliquely fall on the droplet in the reflection optical system, it is difficult to accurately detect diffracted light from the droplet surface. For this reason, accurate measurement cannot be performed. Further, similarly as in the case of the transmission optical system, a distribution of intensity of diffraction pattern is complicated, so that analysis and calculation of a data base require much time.

As described above, in order to perform high-speed and high-accuracy measurement of the droplet arranged on the substrate by a simple means, it is necessary to ensure the perpendicular incidence of the laser light.

A material for detector 5 is not particularly limited so long as the detector 5 can project the diffraction pattern. For example, it is possible to use a method in which the diffraction pattern is projected on a screen formed of a light scattering material and the projected diffraction pattern is picked up by the image pickup apparatus or a method in which a desired area of the diffraction pattern is directly detected by an optical sensor such as a photodiode. As a material for the screen, it is possible to use tracing paper, a diffusion plate, opal glass, etc.

When the diffraction pattern is picked up as an image by using a image pickup apparatus 6, a positional relationship among the laser light source 1, the droplet 4, and the detector 5 is important. Referring to FIG. 1(a), in order to accurately pick up an image of a diffraction pattern by diffracted light generated by causing laser light from the laser light source 1 to perpendicularly enter the droplet 4, the generated diffraction pattern is projected on a screen and the image pickup apparatus 6 may be arranged perpendicularly to the laser light.

When the detector 5 is a transmission type screen, it is possible to pick up the diffraction pattern as an image from a rear surface side of the screen, so that it is possible to arrange the image pickup apparatus 6 perpendicularly to an optical axis. In the case of picking up the image from a front surface side of the screen, it is possible to pick up an image perpendicular to the optical axis by performing image picking up by using a half mirror. However, in other cases, it is difficult to perpendicularly arrange the image pickup apparatus 6. In the case of disposing the image pickup apparatus 6 with respect to a direction other than the perpendicular direction, it is necessary to correct the direction on the basis of an inclination or distance of the image pickup apparatus 6 when the shape of the droplet is obtained from the diffraction pattern. As the image pickup apparatus 6, it is preferable that an image pickup apparatus, having a wide dynamic range with respect to brightness and a variable shutter speed, such as a digital single-lens reflex camera, a CMOS camera, or a CCD camera is used. Further, when a camera having a high frame rate is used as an image pickup means, it is also possible to capture a temporal change of the droplet caused in a very short time, such as a vaporization process of a minute droplet having a contact diameter of 100 μm or less as the member to be measured in the present invention.

As an analyzer (analyzing apparatus) 7, it is possible to use an ordinary personal computer with no problems so long as it can measure a shape feature of an object from a diffraction pattern by inputting therein data for the diffraction pattern from the image pickup apparatus 6.

In order to determine the shape of the object on the substrate from the diffraction pattern detected by the detector or the image pickup apparatus, it is necessary to determine the shape feature of the member to be measured from an analysis result of the diffraction pattern on the basis of optical theory.

As a method of identifying (specifying) the shape of the member to be measured from the diffraction pattern, the following three methods can be considered.

A first method is a method in which all predictable shape features are extracted and objects having the respective shape features are actually prepared and then diffraction patterns from the objects are detected by the above described optical system, stored in a database, and are compared with a diffraction pattern obtained from a droplet.

A second method is a method in which all predictable shape features are extracted and diffraction patterns generated by the above described optical system are calculated based on optical theory, stored in a database, and are compared with a obtained diffraction pattern.

A third method is a method in which a shape feature of a droplet is calculated by calculation based on optical theory for each detected diffraction pattern.

From these methods, depending on a shape of an object or a performance of the analyzer, an optimum method may be selected.

The first method can be performed easily. In this embodiment, by taking the second method as an example, the method of determining the droplet shape from the obtained diffraction pattern will be described.

First, before the shape measurement by the above described optical system used in the present invention is performed, a database is created in advance. In this database, numerical data associating shape features of droplets with diffraction patterns obtained by numerical calculation on the basis of optical theory with respect to the droplets in the case of employing the same conditions as those in actual measurement in terms of refractive indices of the droplets, distances between the droplets and the screen, and the like are stored. In the measurement in this embodiment, it is desirable that pluralities of numerical data corresponding to contact diameters and contact angles are prepared for each refractive index on the assumption that all the members to be measured are droplet shapes. This step of creating the database corresponds to the step S0 shown in FIG. 8.

As described above, the droplet shape measuring method of the present invention quickly performs the shape measurement with a simple constitution, so that the method can be suitably utilized for shape measurement of the minute droplet of 100 μm or less in contact diameter.

Further, in the case where the member to be measured is a readily vaporizable liquid, a resultant diffraction pattern is changed with time. Accordingly, by determining the shape feature of the member to be measured at a time point set at an appropriate time interval, it is also possible to observe the temporal change of the shape of the readily vaporizable member to be measured.

Embodiment 1

Figure 1:
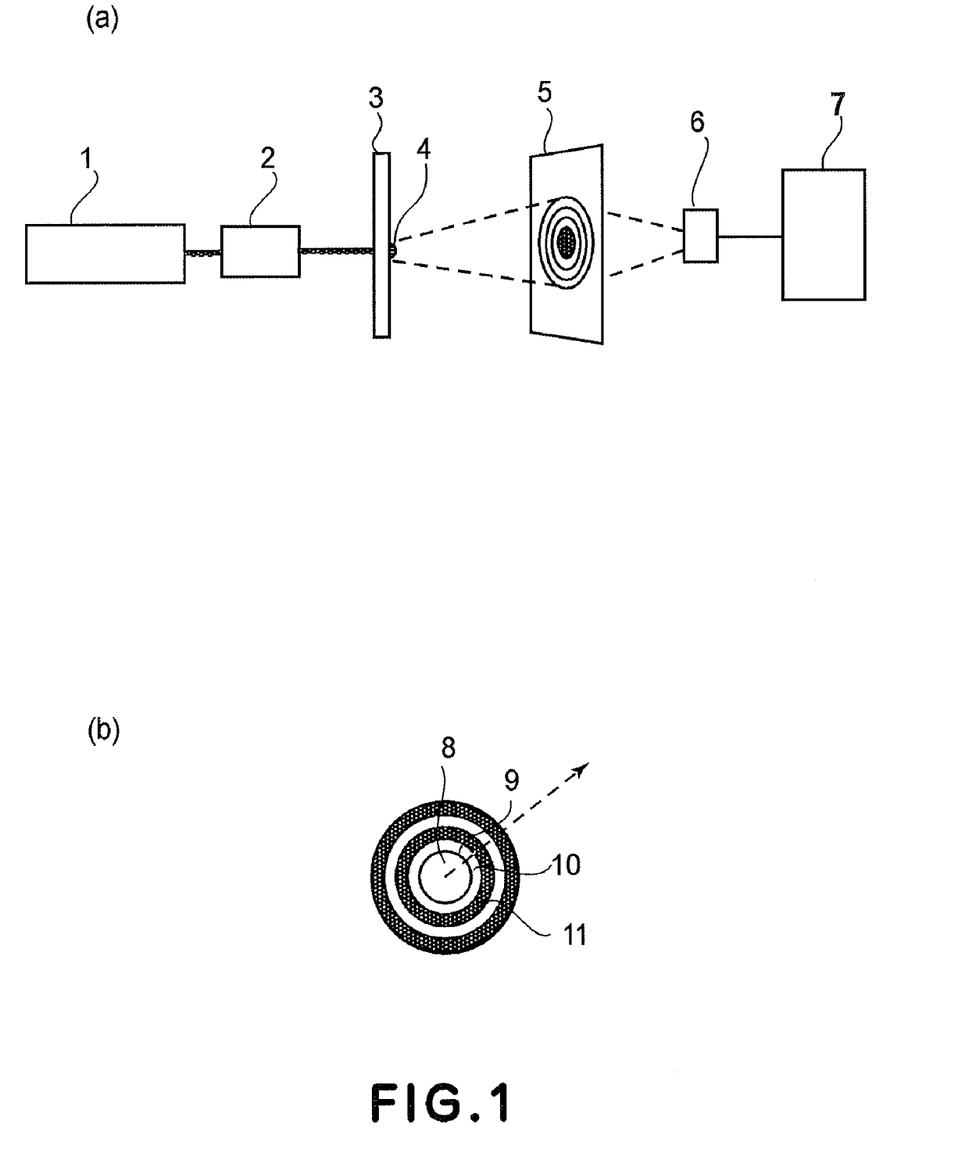
FIG. 1(a) is a schematic view showing a constitution of a droplet shape measuring apparatus and FIG. 1(b) is a schematic view showing a central portion of a diffraction pattern.

FIG. 1(*a*) shows an optical system of a droplet shape measuring apparatus in this embodiment. In this droplet shape measuring apparatus, laser light to be adjusted in beam diameter by an optical system 2 is emitted from a laser light source 1 to enter a substrate 3 having thereon a member to be measured 4 from a rear surface side of the substrate 3 and then a diffraction pattern produced by diffracted light generated by passage of the laser light through the member to be measured 4 is detected by a detector 5. As the detector 5, a transmission type screen is used. An image pickup apparatus 6 is arranged so that an image perpendicular to an optical axis can be obtained from a rear surface side of the detector 5. The image picked up by the image pickup apparatus 6 is subjected to image processing by an analyzer 7, so that a shape feature of the member to be measured 4 is determined.

As the laser light source 1, a He—Ne laser having an emission wavelength of 632.8 nm and an emission diameter of 0.8 mm was used.

The optical system was adjusted so that a laser beam diameter was about 150 μm on the substrate. The optical system for adjusting the laser beam diameter was constituted by a beam expander and a planoconvex lens. The beam expander used in this embodiment was optimized for the emission wavelength of 632.8 nm and had a 3× magnification. The planoconvex lens had a focal distance of 400 nm. By this constitution, the adjustment is made so that the beam diameter is narrowest at a position of the object on the substrate and a phase plane is a horizontal plane with respect to an optical axis.

As the substrate on which the droplet was arranged, a 0.7 mm-thick glass plate was used.

As the member to be measured, an ethylene glycol droplet was used in this embodiment. Ethylene glycol has a refractive index of 1.431 at normal temperature.

As the detector, tracing paper was used as a transmission type screen. In this embodiment, adjustment was made so that an optical axis of the laser light source and the screen were perpendicular to each other. More specifically, for the adjustment, a mirror was attached to a screen holding member and an angle of the screen holding member was adjusted so that return light of the laser light entered a laser light emitting portion.

A distance between the screen and the substrate was 5 cm.

The image pickup apparatus was prepared by mounting a macrolens having a focal distance of 55 mm to a CMOS camera having 1024×1024 pixels. An angle of view (field) was about 50×50 mm and a resolution was about 42 μm/pixel.

On the substrate, a drop ethylene glycol was put by using an ink jet method and thereafter the substrate was placed on the optical axis. A position of the substrate was adjusted so that the ethylene glycol droplet was irradiated with laser light and projection of a diffraction pattern onto the screen 5 was confirmed by eyes. Thereafter, an image of the diffraction pattern was picked up by the image pickup apparatus such as a camera.

Figure 2:
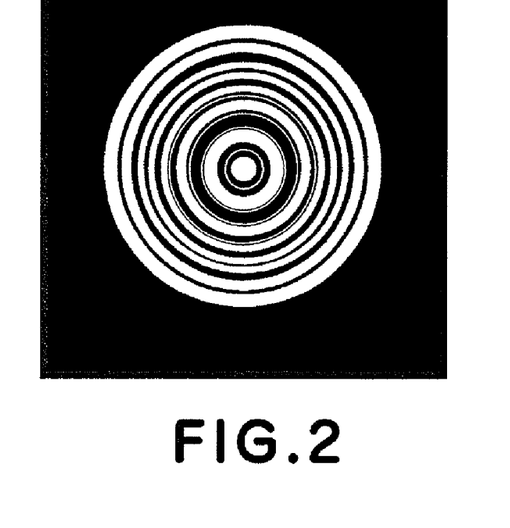
FIG. 2 is a schematic view showing a pattern image of a microlens in Embodiment 1.

FIG. 2 shows the thus picked-up image of the diffraction pattern. As shown in FIG. 2, the diffraction pattern was a pattern of concentric circles.

FIG. 1(b) is a schematic view showing a state of the center and its surrounding portion of the concentric circles of the diffraction pattern image shown in FIG. 2. With a distance from a center 8 of the diffraction pattern as a starting point, a dark portion 9, a bright (light) portion 10, and a dark portion 11 are alternated.

Before the diffraction pattern image was picked up, an optical axis position on the screen was obtained by irradiating only the substrate with the laser light without putting the ethylene glycol droplet on the substrate. With the optical axis position as the center of the diffraction pattern, a brightness with respect to a radial direction, indicated by a dotted arrow shown in FIG. 1(b), which can be appropriately selected with the center of the concentric circles of the diffraction pattern as the starting point was measured. Herein, the dark portion is defined as a fringe position. When fringe positions of the detected diffraction pattern were measured, they were 0.46 mm, 0.8 mm, and 1.22 mm from the center of the concentric circles.

The droplet of ethylene glycol used in this embodiment was a droplet of several tens of picoliters ejected by the ink jet method. The droplet of this size has a contact diameter of 100 μm or less on the substrate. The droplet having a contact diameter of about 100 μm or less is little affected by gravitation, so that a shape feature of the droplet is determined only by a surface tension of the substrate and an internal pressure of the droplet. In such a case, the droplet shape is a part of a sphere. When the droplet shape is the part of the sphere, the droplet shape can be represented by a contact diameter and a contact angle. For this reason, analysis of the diffraction pattern obtained during the irradiation of the droplet with the laser light is easy.

In theory, the diffraction pattern is intrinsic to a shape feature and refractive index of the droplet. Accordingly, only one droplet shape feature can be determined from one diffraction pattern.

In the present invention, it is desirable that the droplet shape is measured by using a database for droplet shape features and diffraction patterns on the basis of a theoretical calculation result.

Figure 3:
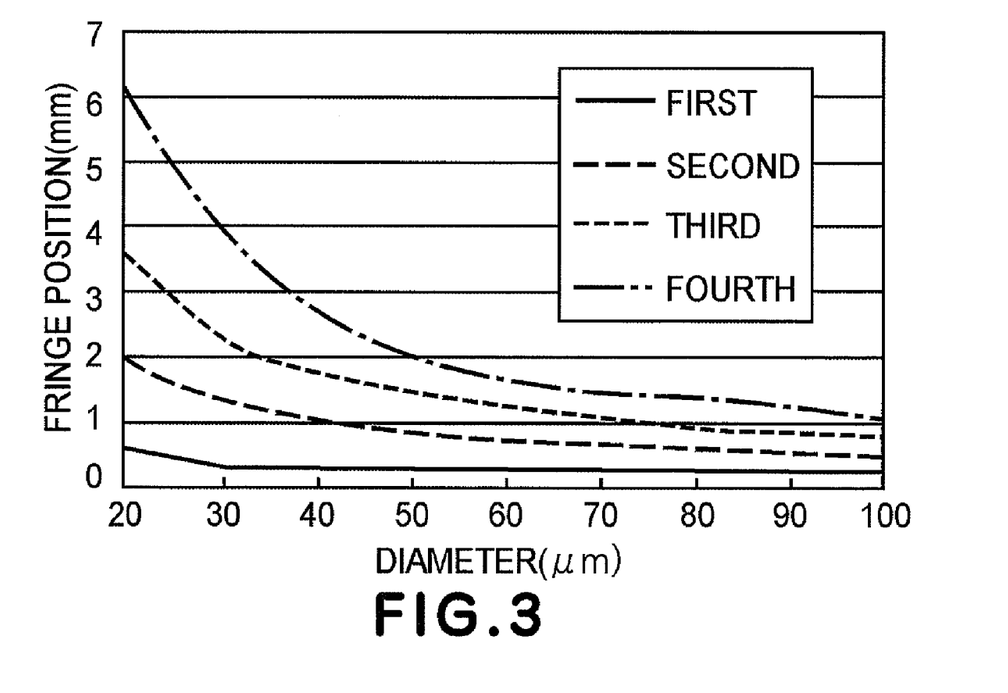
FIG. 3 is a graph showing a relationship between a characteristic length (contact diameter) of an object and a dark-part position of a diffraction pattern in the case where a shape of the object has axial symmetry with respect to a normal to the object.

In this embodiment, a database storing relationships among fringe positions, contact diameters, and contact angles including a relationship as shown in FIG. 3 is prepared and utilized for measuring the shape feature of the ethylene glycol droplet.

FIG. 3 is a graph obtained by calculating a relationship, between a fringe position and a contact diameter of the diffraction pattern obtained in the above constituted droplet shape measuring apparatus, on the basis of optical theory. It has been theoretically known that a fringe position close to the center of the diffraction pattern is less affected by a contact angle and a refractive index. Accordingly, the droplet diameter can be obtained from FIG. 3 irrespective of the refractive index.

In FIG. 3, a relationship between first to fourth fringe positions and contact diameters when dark portion positions are taken as a first (primary) fringe position, a second (secondary) fringe position, . . . , in increasing order of distance from the center of the diffraction pattern.

Based on the relationship between the contact diameters and the fringe positions as shown in FIG. 3, when a contact diameter estimated by the fringe position of the diffraction pattern shown in FIG. 2 was obtained, the contact diameter was about 90 μm. Based on this value, a diffraction pattern was calculated by changing a contact angle with respect to the refractive index of ethylene glycol. When the calculated diffraction pattern and a detected diffraction pattern were compared with each other, a well matched diffraction pattern provided a contact angle of 44-46 degrees.

Accordingly, the shape of the ethylene glycol droplet was considered that it has a contact diameter of about 90 μm and a contact angle of 44-46 degrees.

The ethylene glycol droplet in this embodiment was vaporized in several seconds. When the shape feature of the ethylene glycol droplet was measured at appropriate time intervals with a change in diffraction pattern with time, it was possible to measure changes with time of the contact diameter and the contact angle. Accordingly, by using the apparatus of this embodiment, it is also possible to observe the process of the change in shape during the vaporization of the droplet.

Embodiment 2

By using the same optical system as that used in Embodiment 1, shape measurement of a microlens was performed. The microlens is equivalent to the droplet in terms of a shape feature, so that the shape measurement of the microlens can be performed by the same theory. Further, the microlens causes no shape change with time, different from the droplet, so that it is possible to perform the shape measurement by another measuring method. By comparing a measurement result by another measuring method with a measurement result by the same measuring method as in Embodiment 1, it is possible to prove certainty of measurement.

When a refractive index of the microlens was measured by using an optical measuring method, it was 1.596 with respect to a laser wavelength employed.

Figure 4:
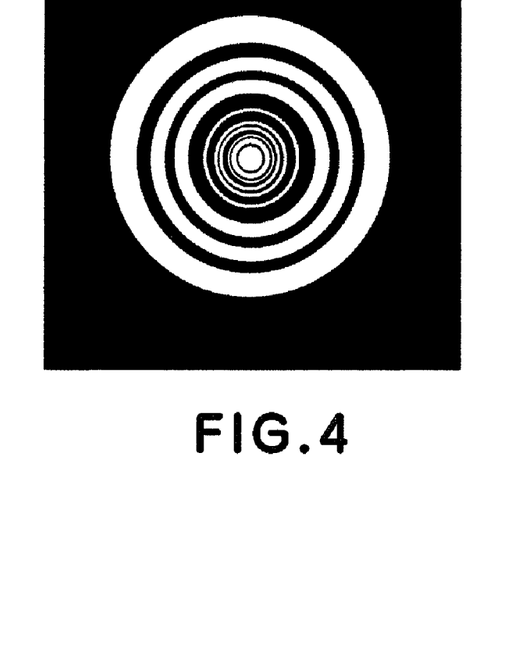
FIG. 4 is a schematic view showing a pattern image of a microlens in Embodiment 2.

With respect to the microlens formed on a substrate, diffraction pattern was obtained by the same procedure as in Embodiment 1. FIG. 4 shows the diffraction pattern obtained from the microlens. When fringe positions were measured, they were 1.5 mm, 2.3 mm, and 3.6 mm from the center of the diffraction pattern.

The diffraction pattern provided a contact diameter of about 30 μm and a contact angle of about 29 or 30 degrees.

Accordingly, the shape of the microlens measured in this embodiment can be said that the shape is about 30 μm in contact diameter and about 29 or 30 degrees in contact angle.

In order to confirm certainty of the measurement result, when the shape feature of the microlens was measured through a confocal microscope, the contact diameter was 31.2 μm and the contact angle was 28.1 degrees. These values closely match with those measured in this embodiment.

Embodiment 3

FIG. 5 shows an embodiment of a constitution of an apparatus for measuring a diffraction pattern by a reflection optical system.

This droplet shape measuring apparatus causes laser light emitted from a laser light source 21 to perpendicularly enter a droplet-shaped member to be measured 4 by adjusting the laser light so as to have an equiphase wave surface parallel to an optical axis. The laser light entering the member to be measured 4 passes through the member to be measured 4, reflected by a substrate 3, and is come out of the member to be measured 4. During this process, the laser light is out of phase depending on the shape of the droplet-shaped member to be measured 4, so that a diffraction pattern is generated. This diffraction pattern is detected by a detector 5 and picked up as an image by an image pickup apparatus 6. A combination of the detector 5 with the image pickup apparatus 6 may be combination consisting of a screen, such as tracing paper, for simply projecting the diffraction pattern thereon and an ordinary image pickup means such as camera. It is also possible to directly record the diffraction pattern as an image by using an area sensor as the detector 5.

In this embodiment, in order to arrange the screen as the detector 5 perpendicularly to the optical axis, the screen is provided with a hole through which the laser light passes as a center of the screen.

As the laser light source 1, a He—Ne laser having an emission wavelength of 632.8 nm was used.

The optical system was set so that a laser beam diameter was about 150 μm at an incident position on the member to be measured 4. The optical system for adjusting the laser beam diameter was constituted by a beam expander and a planoconvex lens. The beam expander used in this embodiment was optimized for the emission wavelength of 632.8 nm and had a 3× magnification. The planoconvex lens had a focal distance of 400 nm. By this constitution, the adjustment is made so that the beam diameter is narrowest at a position of the object on the substrate and a phase plane is a horizontal plane with respect to an optical axis.

As the member to be measured in this embodiment, a microlens different from that used in Embodiment 2 was used.

As the detector, tracing paper was used as a transmission type screen. In this embodiment, adjustment was made so that an optical axis of the laser light source and the screen were perpendicular to each other.

A distance between the screen and the substrate was 8 cm.

As the image pickup apparatus, a digital single-lens reflex camera having 3504×2336 pixels was used. An angle of view (field) was about 70×47 mm and a resolution was about 20 μm/pixel.

The image pickup apparatus is arranged at an inclination angle of 20 degrees with respect to the optical axis.

The substrate on which the microlens was arranged was placed on the optical axis and it was confirmed by eyes that the diffraction pattern was obtained. Thereafter, an image of the diffraction pattern was picked up by the camera.

Figure 6:
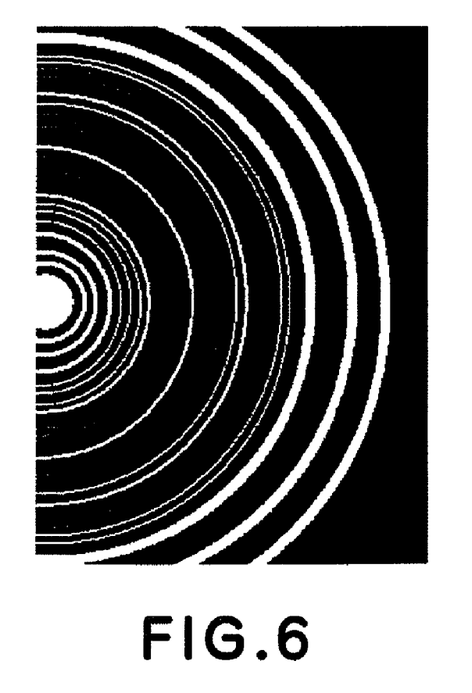
FIG. 6 is a schematic view showing a pattern image of a microlens in Embodiment 3.

FIG. 6 shows a right half of the thus picked-up image of the diffraction pattern. As shown in FIG. 6, the diffraction pattern was a pattern of concentric circles. When distances of fringe positions from the center of the diffraction pattern were measured, they were 0.28 mm, 0.44 mm, and 0.74 mm. In this embodiment, a graph showing a relationship between fringe positions and contact diameters for the droplet shape measuring apparatus in this embodiment is prepared in advance. A contact diameter obtained from the measured fringe positions was about 49 μm. Further, similarly as in the case of the transmission optical system, a diffraction pattern was calculated by using a theoretical calculation with respect to the obtained contact diameter of 49 μm and compared with the measurement result. As a result, a well-matched diffraction pattern had a contact angle of about 34-37 degrees.

When the shape feature of the microlens was measured through a confocal microscope, the contact diameter was 51.3 μm and the contact angle as 35.5 degrees. These values are very close to those measured in this embodiment.

Embodiment 4

In order to compare measurement results between the reflection optical system and the transmission optical system, the microlens used in Embodiment 3 was subjected to shape measurement by using the same transmission optical system as in Embodiment 1.

Figure 7:
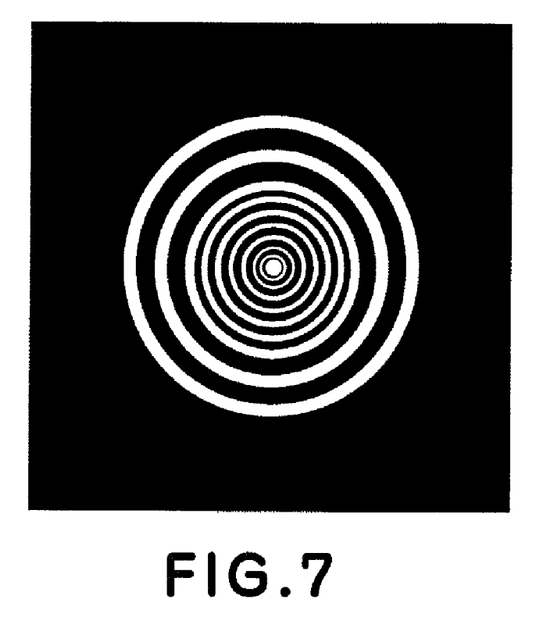
FIG. 7 is a schematic view showing a pattern image of an ethylene glycol droplet in Embodiment 1.

FIG. 7 shows a diffraction pattern obtained in this embodiment. Similarly as in Embodiment 1, when distances of fringe positions from the center of the diffraction pattern were measured, they were 0.83 mm, 1.33 mm, and 2.12 mm. By using these fringe positions, when a contact diameter was obtained from a graph, the contact diameter was about 50 μm. The contact angle was measured as about 35-36 degrees. These results are substantially identical to those for the reflection optical system and also closely match with the measurement results obtained by the confocal microscope.

While the invention has been described with reference to the structures disclosed herein, it is not confined to the details set forth and this application is intended to cover such modifications or changes as may come within the purpose of the improvements or the scope of the following claims.

This application claims priority from Japanese Patent Application No. 197591/2006 filed Jul. 20, 2006, which is hereby incorporated by reference.

What is claimed is:

1. A droplet shape measuring method comprising:
   a first step of detecting a diffraction pattern produced by mutual interference between diffracted light generated when a substrate is perpendicularly irradiated with laser light so that a droplet arranged on the substrate is irradiated with the laser light; and
   a second step of measuring a shape feature of the droplet from a refractive index of the droplet and the detected diffraction pattern.

2. A method according to claim 1, wherein the droplet has a contact diameter of 100 μm or less.

3. A method according to claim 1, wherein in said second step, the shape feature of the droplet is measured by comparing the detected diffraction pattern with a diffraction pattern, obtained when a diffraction pattern is generated under the same condition as that in said first step, associated with a shape feature of a droplet.

4. A method according to claim 1, wherein in said second step, the shape feature of the droplet is measured by associating the detected diffraction pattern with a shape feature of a droplet on the basis of optical theory.

5. A droplet shape measuring apparatus comprising:
   an optical system for generating a diffraction pattern from diffracted light from a droplet by perpendicularly irradiating the droplet arranged on a substrate with laser light; and
   a detector for detecting the generated diffraction pattern,
   wherein a shape feature of the droplet is measured from a refractive index of the droplet and the diffraction pattern.

* * * * *